(12) United States Patent
Zhai et al.

(10) Patent No.: US 10,420,528 B2
(45) Date of Patent: Sep. 24, 2019

(54) METHOD AND DEVICE FOR DETECTING VISCOELASTIC PARAMETER OF VISCOELASTIC MEDIUM

(71) Applicant: WUXI HISKY MEDICAL TECHNOLOGIES CO., LTD., Wuxi (CN)

(72) Inventors: Fei Zhai, Wuxi (CN); Jinhua Shao, Wuxi (CN); Jin Sun, Wuxi (CN); Houli Duan, Wuxi (CN); Qiang Wang, Wuxi (CN)

(73) Assignee: WUXI HISKY MEDICAL TECHNOLOGIES CO., LTD., Jiangsu (CN)

( * ) Notice: Subject to any disclaimer, the term of this patent is extended or adjusted under 35 U.S.C. 154(b) by 0 days.

(21) Appl. No.: 16/012,702

(22) Filed: Jun. 19, 2018

(65) Prior Publication Data
US 2018/0296181 A1 Oct. 18, 2018

Related U.S. Application Data

(63) Continuation of application No. PCT/CN2016/103645, filed on Oct. 27, 2016.

(30) Foreign Application Priority Data

Dec. 24, 2015 (CN) .......................... 2015 1 0993421

(51) Int. Cl.
*A61B 8/00* (2006.01)
*A61B 8/08* (2006.01)
(Continued)

(52) U.S. Cl.
CPC ............ *A61B 8/085* (2013.01); *A61B 5/0051* (2013.01); *A61B 5/4244* (2013.01);
(Continued)

(58) Field of Classification Search
CPC ....... A61B 8/085; A61B 8/5207; A61B 8/485; A61B 8/08; A61B 8/00
See application file for complete search history.

(56) References Cited

U.S. PATENT DOCUMENTS

| | | | | |
|---|---|---|---|---|
| 2008/0249408 | A1* | 10/2008 | Palmeri | A61B 8/08 600/438 |
| 2010/0069751 | A1* | 3/2010 | Hazard | A61B 5/415 600/438 |

(Continued)

FOREIGN PATENT DOCUMENTS

| | | |
|---|---|---|
| CN | 101699280 A | 4/2010 |
| CN | 102078205 A | 6/2011 |

(Continued)

OTHER PUBLICATIONS

The Canadian Examination Report of corresponding Candian patent application No. 3,009,241, dated Sep. 14, 2018.
(Continued)

*Primary Examiner* — Joel Lamprecht
(74) *Attorney, Agent, or Firm* — J.C. Patents

(57) ABSTRACT

Disclosed is a method and device for detecting a viscoelastic parameter of a viscoelastic medium. The method comprises: applying a mechanical vibration at a single predetermined frequency to the viscoelastic medium to generate a shear wave in the viscoelastic medium (101); emitting ultrasonic waves to the viscoelastic medium, and receiving ultrasonic echo signals (102); acquiring maximum displacement data of the shear wave at various depths according to the ultrasonic echo signals (103), each of the maximum displacement data representing a maximum oscillation amplitude of the shear wave when the shear wave propagates to different depths in the viscoelastic medium; fitting each of the maximum displacement data to obtain a maximum displacement attenuation curve (104); and determining the viscoelastic
(Continued)

parameter of the viscoelastic medium according to the maximum displacement attenuation curve (105). The method and device can provide a more accurate measurement result of tissue fibrosis.

12 Claims, 5 Drawing Sheets

(51) Int. Cl.
 *A61B 5/00* (2006.01)
 *G01S 7/52* (2006.01)
 *G01S 15/89* (2006.01)

(52) U.S. Cl.
 CPC .............. *A61B 5/7225* (2013.01); *A61B 8/08* (2013.01); *A61B 8/485* (2013.01); *A61B 8/5207* (2013.01); *G01S 7/52042* (2013.01); *G01S 7/52079* (2013.01); *G01S 15/899* (2013.01); *G01S 15/8911* (2013.01)

(56) References Cited

U.S. PATENT DOCUMENTS

| | | | |
|---|---|---|---|
| 2010/0222678 A1 | 9/2010 | Bercoff et al. | 600/442 |
| 2012/0215101 A1 | 8/2012 | Maleke et al. | 600/438 |
| 2013/0317362 A1* | 11/2013 | Shi | A61B 5/0051 600/438 |
| 2013/0345565 A1* | 12/2013 | Fan | A61B 8/08 600/442 |
| 2014/0088421 A1 | 3/2014 | Guzina et al. | 600/438 |
| 2015/0133783 A1* | 5/2015 | Tabaru | A61B 8/485 600/438 |

FOREIGN PATENT DOCUMENTS

| | | |
|---|---|---|
| CN | 103054552 A | 4/2013 |
| CN | 104434216 A | 3/2015 |
| CN | 104825195 A | 8/2015 |
| CN | 105455851 A | 4/2016 |
| JP | 2012-170823 A | 9/2012 |
| KR | 10-1914021 B1 | 10/2018 |
| RU | 2013 133 827 A | 1/2015 |
| WO | 2007083745 A1 | 7/2007 |
| WO | WO 2015/116893 A1 | 8/2015 |

OTHER PUBLICATIONS

The International Search Report of corresponding International PCT Application No. PCT/CN2016/103645, dated Jan. 26, 2017.
The Chinese Examination Report and Search Report of corresponding China patent application No. 201510993421.3, dated Nov. 23, 2017.
The Russian Federation Examination Report, including search report of corresponding Russian application No. 2018126777/14(042519), dated Jan. 16, 2019.
The Japanese Examination Report Report of corresponding Japanese application No. 2018-532567, dated Jun. 12, 2019.

* cited by examiner

METHOD AND DEVICE FOR DETECTING VISCOELASTIC PARAMETER OF VISCOELASTIC MEDIUM

CROSS-REFERENCE TO RELATED APPLICATION

This application is a continuation of International Application No. PCT/CN2016/103645, filed on Oct. 27, 2016, which claims the priority benefit of China Patent Application No. 201510993421.3, filed on Dec. 24, 2015. The contents of the above identified applications are incorporated herein by reference in their entirety.

TECHNICAL FIELD

The invention belongs to the field of medical technology, and in particular relates to a method and device for detecting a viscoelastic parameter of a viscoelastic medium.

BACKGROUND

Liver fibrosis is usually caused by excessive deposition of extracellular matrix proteins and often appears in most types of patients of chronic liver disease. Since early liver fibrosis or liver cirrhosis is reversible or controllable, an accurate and effective early diagnosis of liver fibrosis is essential.

Shear wave elastography can quantitatively assess the degree of liver fibrosis and liver cirrhosis by measuring liver stiffness values. The most widely used in clinical non-invasive liver fibrosis grading detection is the transient elastography.

Since the liver is a viscoelastic body, i.e., a viscoelastic medium, and changes in its viscoelastic parameter is closely related to a variety of liver diseases, liver viscoelasticity parameter can provide very valuable information for the early diagnosis of liver fibrosis.

At present, a measurement of a tissue is mainly to measure an elastic parameter of the tissue, while ignore a viscosity parameter, i.e., viscoelastic parameter of the tissue, which has an adverse effect on detection results of an early lesion of tissues, such as liver fibrosis.

SUMMARY

In view of the problems existing in the prior art, the present invention provides a method and device for detecting a viscoelastic parameter of a viscoelastic medium, which is used to acquire a viscoelastic parameter of the tissue so as to improve accuracy of a measurement result of fibrosis degree.

The present invention provides a method for detecting a viscoelastic parameter of a viscoelastic medium, comprising:
applying a mechanical vibration at a single predetermined frequency to the viscoelastic medium to generate a shear wave in the viscoelastic medium;
during propagation of the shear wave in the viscoelastic medium, emitting single-source ultrasonic waves to the viscoelastic medium and receiving ultrasonic echo signals;
acquiring maximum displacement data of the shear wave at various depths according to the ultrasonic echo signals, each of the maximum displacement data representing a maximum oscillation amplitude of the shear wave when the shear wave propagates to different depths in the viscoelastic medium;
fitting each of the maximum displacement data to obtain a maximum displacement attenuation curve;
determining the viscoelastic parameter of the viscoelastic medium according to the maximum displacement attenuation curve.

The present invention provides a device for detecting a viscoelastic parameter of a viscoelastic medium, comprising:
a control host and a probe, the probe including a vibrator and an ultrasonic transducer, wherein
the vibrator, under the control of the control host, applies a mechanical vibration at a single predetermined frequency to the viscoelastic medium, to generate a shear wave in the viscoelastic medium;
during propagation of the shear wave in the viscoelastic medium, the ultrasonic transducer, under the control of the control host, emits single-source ultrasonic waves to the viscoelastic medium and receives ultrasonic echo signals; and
the control host comprises:
a first acquiring module that is configured to acquire maximum displacement data of the shear wave at various depths according to the ultrasonic echo signals, each of the maximum displacement data representing a maximum oscillation amplitude of the shear wave when the shear wave propagates to different depths in the viscoelastic medium;
a computing module that is configured to fit the maximum displacement data to obtain a maximum displacement attenuation curve; and
a first determining module that is configured to determine the viscoelastic parameter of the viscoelastic medium according to the maximum displacement attenuation curve.

In the device for detecting a viscoelastic parameter of the viscoelastic medium provided by the present invention, application of a mechanical vibration at a single predetermined frequency to the tissue only generate a shear wave having a single frequency in the viscoelastic medium. After acquiring the displacement data of the shear wave, each of the maximum displacement data representing the maximum oscillation amplitude of the shear wave when the shear wave propagates to different depths is calculated based on the displacement data, and then the maximum displacement attenuation curve of the shear wave is obtained by fitting each of the maximum displacement data, thereby determining the viscoelastic parameter of the viscoelastic medium according to the maximum displacement attenuation curve. The viscoelastic parameter is related to both elasticity and viscosity. With this embodiment, it is possible to acquire a viscoelastic parameter related to both elasticity and viscosity and increase measurement dimension of the tissue, which is beneficial to provide richer tissue parameter information and measurement dimensions as well as helpful to provide more accurate measurement result of tissue fibrosis.

DESCRIPTION OF EMBODIMENTS

Figure 1:
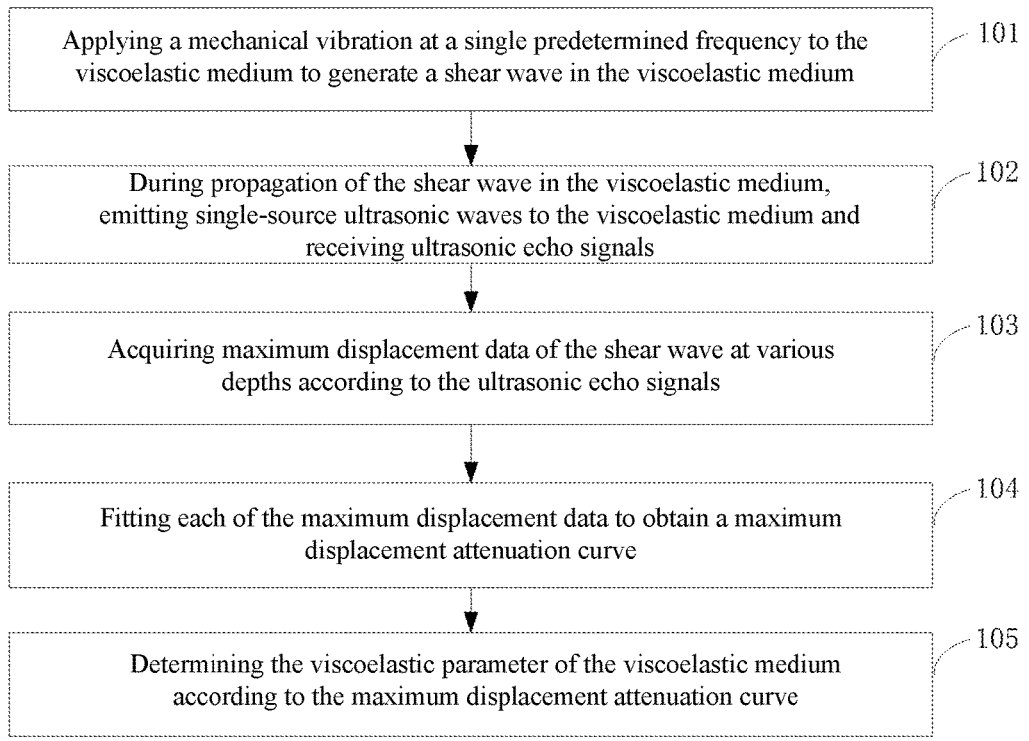
FIG. 1 is a flow chart of a first embodiment of a method for detecting a viscoelastic parameter of the viscoelastic medium according to the present invention.

FIG. 1 is a flow chart of a first embodiment of a method for detecting a viscoelastic parameter of the viscoelastic medium according to the present invention. The method provided in this embodiment is mainly used to detect a viscoelastic parameter of a liver tissue, which may be performed by a detection device. The detection device may be an existing non-invasive liver fibrosis detector with a processing function required to perform the method described in this embodiment having been added. The detection device mainly includes a control host and a probe. The probe includes a vibrator for generating mechanical vibration and an ultrasonic transducer for emitting and receiving ultrasonic waves.

As shown in FIG. 1, the method for detecting a viscoelastic parameter of the viscoelastic medium may include following steps:

Step 101: Apply a mechanical vibration at a single predetermined frequency to the viscoelastic medium to generate a shear wave in the viscoelastic medium.

In the present embodiment, detection of the viscoelastic parameter of the liver tissue is taken as an example. The liver tissue here is the above-mentioned viscoelastic medium. Applying a mechanical vibration at a single predetermined frequency to the viscoelastic medium refers to applying the mechanical vibration to skin surface corresponding to the liver tissue.

Specifically, the vibrator applies a sinusoidal mechanical vibration perpendicular to the skin surface on the skin surface, thereby generating a corresponding shear wave in the liver tissue, and the shear wave propagates in the liver tissue. The frequency of the mechanical vibration may be, for example, a low frequency such as 50 Hz.

Step 102: During the propagation of the shear wave in the viscoelastic medium, emit single-source ultrasonic waves to the viscoelastic medium and receive ultrasonic echo signals.

In the present embodiment, the ultrasonic transducer emits low-frequency single source ultrasonic signals to the liver tissue at the position where the vibrator applies the mechanical vibration, and receives ultrasonic echo signals.

Wherein, multiple-frame ultrasonic signals can be emitted to the liver tissue at a certain time interval to track propagation process of shear waves in the liver tissue.

For example, after the shear wave has been generated by applying the mechanical vibration, and during a certain period of time when the shear wave is propagating in the viscoelastic medium, a series of ultrasonic signals are emitted through a transmitter of the single source ultrasonic module integrated on the vibration probe and ultrasonic echo signals are received. By processing ultrasonic echo signals data during this period of time, strain and displacement data information of the medium on an ultrasonic scan line during this period of time can be acquired.

In the embodiment of the present invention, only the displacement data is taken for illustration. It can be appreciated that the strain data can similarly refer to the displacement data, and has the same processing method as the displacement data, thus it will not be described again.

Step 103: Acquire maximum displacement data of the shear wave at various depths according to the ultrasonic echo signals.

Wherein, each of the maximum displacement data represents a maximum oscillation amplitude of the shear wave when the shear wave propagates to different depths in the viscoelastic medium.

As described above, the ultrasonic echo signals can reflect propagation displacement of the shear wave in liver tissue. Therefore, displacement data of the shear wave can be acquired based on the ultrasonic echo signals. In order to ensure accuracy of the displacement data, a certain digital signal processing may be performed on the ultrasonic echo signals. The signal processing includes at least one of the following signal processings: time domain cross correlation, spectral cross correlation, square error sum, speckle tracking, scale invariant feature point tracking, dynamic programming, zero cross tracking, and peak search.

Figure 2:
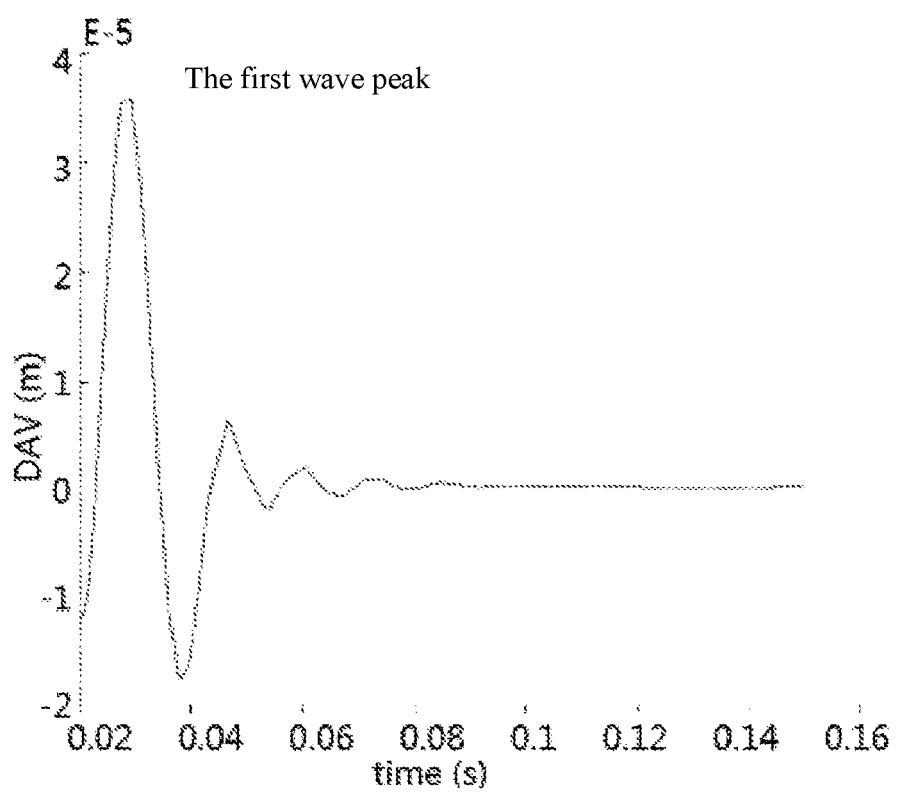
FIG. 2 is a schematic diagram of displacement data when the shear wave propagates to a certain depth.

In order to visually explain the displacement data of the shear wave, FIG. 2 shows a time-varying displacement curve of the shear wave that is generated by mechanical vibration of an external probe and propagates at a fixed depth within the tissue. In this embodiment, a mechanical vibration perpendicular to the liver tissue is applied to the liver tissue, and the ultrasonic transducer captures a displacement perpendicular to an axis of the liver tissue at a position where the mechanical vibration is applied, that is, a longitudinal displacement. DAV shown in FIG. 2 represents the longitudinal displacement.

It can be seen from FIG. 2 that the displacement data exhibits an oscillation attenuation characteristic at a fixed depth. In general, the maximum displacement occurs at the first wave peak. Therefore, the maximum displacement data can be extracted from the displacement data acquired at corresponding depths, thereby obtaining maximum displacement data at different depths.

Step 104: Fit each of the maximum displacement data to obtain a maximum displacement attenuation curve.

Step 105: Determine a viscoelastic parameter of the viscoelastic medium based on the maximum displacement attenuation curve.

In the present embodiment, different data fitting methods such as polynomial fitting and exponential fitting may be used to fit the acquired maximum displacement data so as to obtain the maximum displacement attenuation curve.

In the process of fitting, in order to ensure the accuracy of the fitting result, a certain data processing can be performed on each of the maximum displacement data.

Optionally, a filtering processing on each of the maximum displacement data in the time domain and frequency domain may be performed, and an abnormal datum in each of the maximum displacement data may be excluded. The abnormal datum may include such a displacement datum that is greater than an average displacement value of all maximum displacement values or greater than a certain multiple of the average displacement value, or the abnormal datum includes such a displacement datum that the difference between the displacement datum and the average displacement value is greater than a certain multiple of standard deviation.

Afterwards, a polynomial fitting is performed on each of the maximum displacement data after excluding the abnormal datum, to obtain the maximum displacement attenuation curve.

Upon a large number of experiments, it is shown that the quadratic polynomial fitting has the best fitting effect. Therefore, a fitting formula is as follows:

$$y = ax^2 + bx + c$$

For the measurement of a certain viscoelastic medium, as a result, the fitting can obtain three parameters including a, b and c. Since the parameters b and c affect the position of the quadratic polynomial curve and have no correlation with the curve attenuation trend and pattern, the parameter a can be extracted to characterize the attenuation trend and pattern of the maximum displacement attenuation curve. This coefficient is commonly determined by both viscosity and the elasticity, and is a viscoelastic parameter. That is, the coefficient corresponding to the highest power variable of the maximum displacement attenuation curve is determined as the viscoelastic parameter of the viscoelastic medium.

In the present embodiment, the low-frequency vibration with a single frequency is used, and the viscoelastic parameter of the measured tissue can be acquired by analyzing the oscillation amplitude of the shear wave. The specific principle is: the oscillation amplitude is related not only to the elastic parameter but also to the viscosity, that is, related to the viscoelastic parameter, which can be described by the wave peak and amplitude attenuation at a specific depth. The descending curve formed by the decrease of the wave peak with increase of the propagation depth is affected by the elasticity and the viscosity. The higher the viscosity is, the smaller the first wave peak in the shallower tissue is, and as the depth deepens, the high-viscosity tissue declines more slowly, while the first wave peak value of the low-viscosity tissue is greater and declines more dramatically.

In the present embodiment, applying mechanical vibration at a predetermined frequency to the tissue generates the shear wave only with a single frequency in the viscoelastic medium. After acquiring the displacement data of the shear wave, the maximum displacement data representing the maximum oscillation amplitude when the shear wave propagates to different depths is calculated based on the displacement data, and then the maximum displacement attenuation curve of the shear wave is obtained by fitting each maximum displacement datum. The viscoelastic parameter of the viscoelastic medium is determined according to the maximum displacement attenuation curve, and is related to both elasticity and viscosity. With this embodiment, it is possible to acquire the viscoelastic parameter related to both elasticity and viscosity and increase the measurement dimension of the tissue, which is beneficial to provide richer tissue parameter information and measurement dimensions as well as helpful to provide more accurate measurement result of tissue fibrosis.

Figure 3:
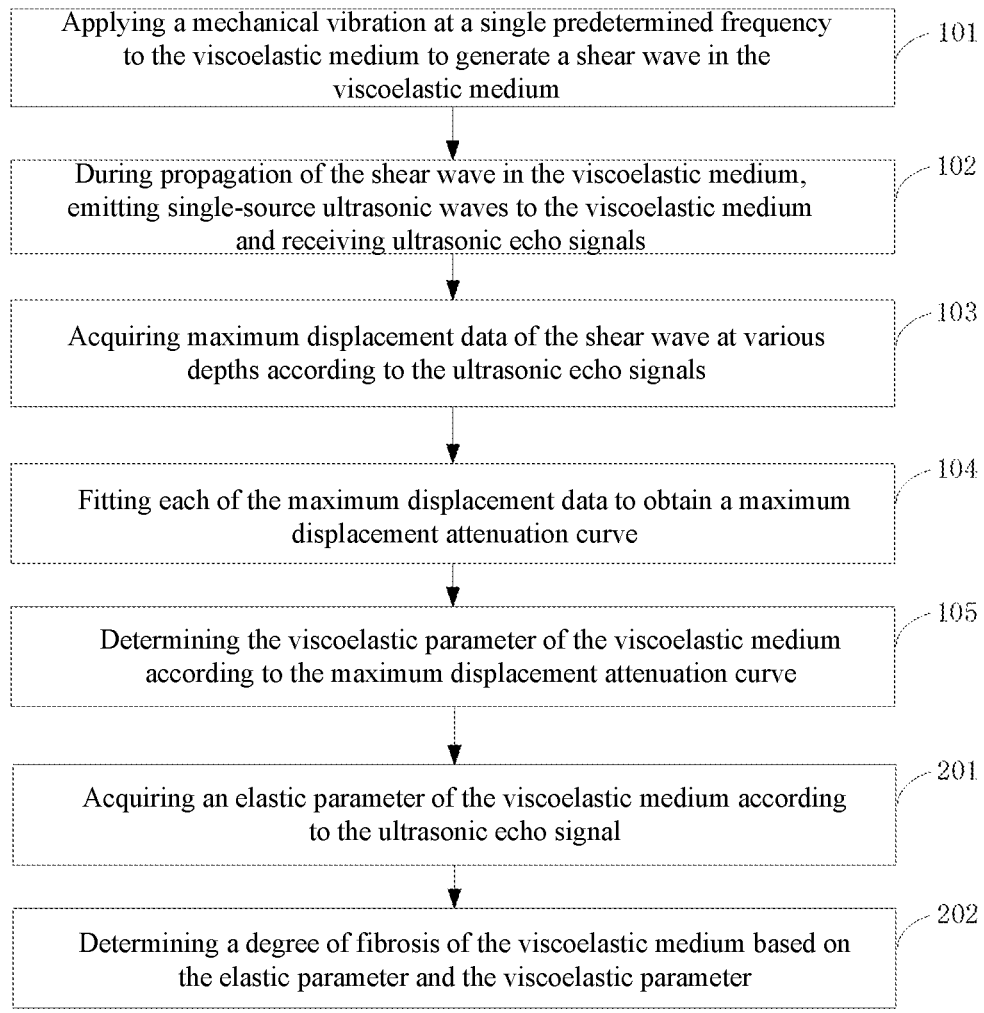
FIG. 3 is a flow chart of a second embodiment of a method for detecting a viscoelastic parameter of the viscoelastic medium according to the present invention.

FIG. 3 is a flow chart of a second embodiment of a method for detecting a viscoelastic parameter of the viscoelastic medium according to the present invention. As shown in FIG. 3, on the basis of the embodiment shown in FIG. 1 and after step 105, it further comprises the following steps:

Step 201: Acquire an elastic parameter of the viscoelastic medium according to the ultrasonic echo signals.

Step 202: Determine a degree of fibrosis of the viscoelastic medium based on the elastic parameter and the viscoelastic parameter.

In the present embodiment, the elastic parameter of the viscoelastic medium can be obtained based on the analysis and processing of the received ultrasonic echo signals via a method in the prior art.

Furthermore, the degree of fibrosis of the tissue is jointly determined by the obtained elastic parameter and the viscoelastic parameter.

For example, at present, the degree of fibrosis of the tissue is generally divided coarsely as serious, general, and not serious and each degree corresponds to a different range of the elastic parameter. On the basis of obtaining the viscoelastic parameter, available data dimensions are provided for further fine division of the degree of fibrosis and accurate determination of the degree of fibrosis.

Figure 4:
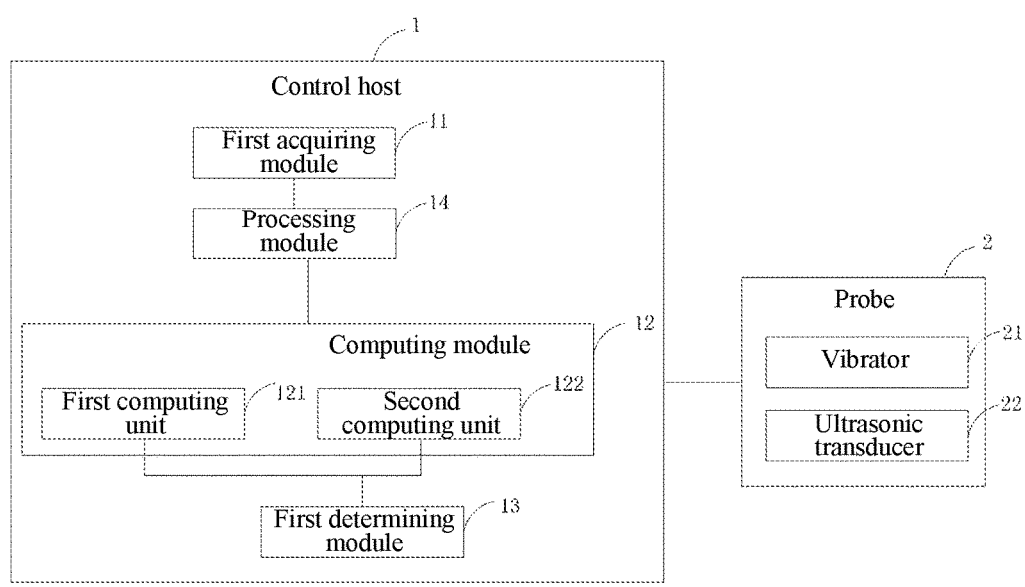
FIG. 4 is a schematic diagram of a first embodiment of a device for detecting a viscoelastic parameter of the viscoelastic medium according to the present invention.

FIG. 4 is a schematic diagram of a first embodiment of a device for detecting a viscoelastic parameter of the viscoelastic medium according to the present invention. As shown in FIG. 4, the device comprises:

a control host 1 and a probe 2. The probe 2 includes a vibrator 21 and an ultrasonic transducer 22.

The vibrator 21, under the control of the control host 1, applies mechanical vibration at a single predetermined frequency to the viscoelastic medium, to generate a shear wave in the viscoelastic medium.

During propagation of the shear wave in the viscoelastic medium, the ultrasonic transducer 22, under the control of the control host 1, emits single-source ultrasonic waves to the viscoelastic medium and receives ultrasonic echo signals.

The control host 1 comprises a first acquiring module 11, a computing module 12, and a first determining module 13.

The first acquiring module 11 is configured to acquire maximum displacement data of the shear wave at various depths according to the ultrasonic echo signals, each of the maximum displacement data representing a maximum oscillation amplitude of the shear wave when the shear wave propagates to different depths in the viscoelastic medium.

The computing module 12 is configured to fit the maximum displacement data to obtain a maximum displacement attenuation curve.

The first determining module 13 is configured to determine the viscoelastic parameter of the viscoelastic medium according to the maximum displacement attenuation curve.

Further, the control host further comprises: a processing module 14.

The processing module 14 is configured to perform at least one of the following signal processings on the ultrasonic echo signals: time domain cross correlation, spectral cross correlation, square error sum, speckle tracking, scale invariant feature point tracking, dynamic programming, zero cross tracking, and peak search.

Specifically, the computing module 12 comprises: a first computing unit 121 and a second computing unit 122.

The first computing unit 121 is configured to perform a filtering processing on each of the maximum displacement data in time domain and frequency domain, to exclude an abnormal datum in each of the maximum displacement data.

The second computing unit 122 is configured to perform a polynomial fitting on each of the maximum displacement data after excluding the abnormal datum, to obtain the maximum displacement attenuation curve.

Specifically, the first determining module 13 is specifically configured to:

determine that the coefficient corresponding to the highest power variable of the maximum displacement attenuation curve is the viscoelastic parameter of the viscoelastic medium.

The detection device in the present embodiment may be configured to execute the technical solution of the method embodiment shown in FIG. 1, and has similar implementation principle and technical effects thereto and are not described herein again.

Figure 5:
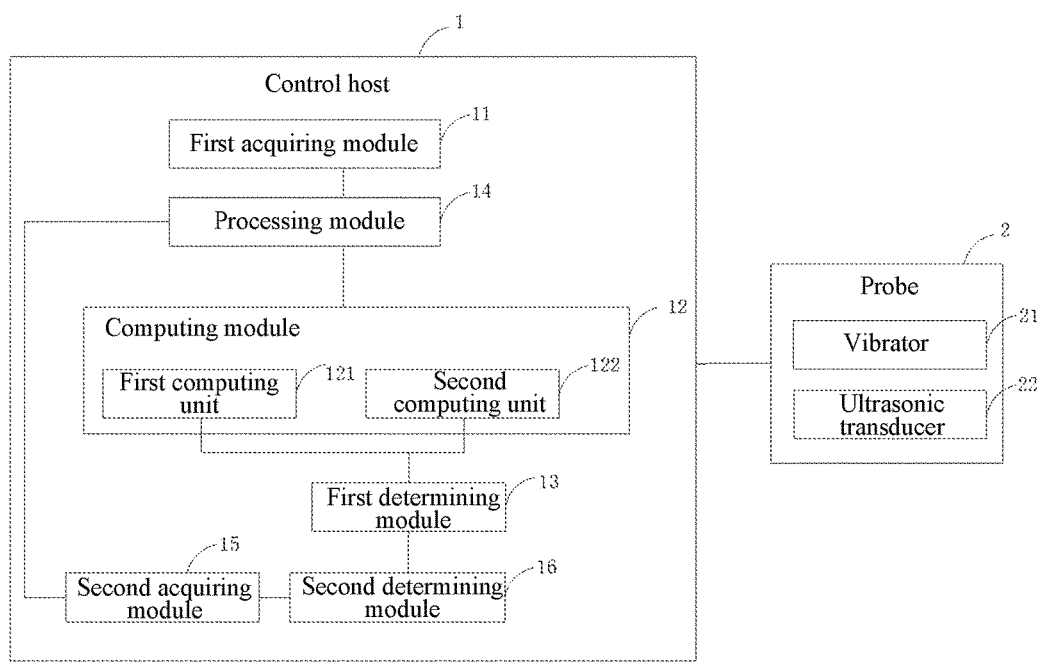
FIG. 5 is a schematic diagram of a second embodiment of a device for detecting a viscoelastic parameter of the viscoelastic medium according to the present invention.

FIG. 5 is a schematic diagram of a second embodiment of a device for detecting a viscoelastic parameter of the viscoelastic medium according to the present invention. As shown in FIG. 5, on the basis of the embodiment illustrated in FIG. 4, the control host 1 further comprises: a second acquiring module 15 and a second determining module 16.

The second acquiring module 15 is configured to acquire the elastic parameter of the viscoelastic medium according to the ultrasonic echo signals.

The second determining module 16 is configured to determine the degree of fibrosis of the viscoelastic medium based on the elastic parameter and the viscoelastic parameter.

The detection device in the present embodiment may be configured to execute the technical solution of the method embodiment shown in FIG. 3, and has similar implementation principle and technical effects thereto and are not described herein again.

Those of ordinary skill in the art can understand that all or part of the steps for implementing the above method embodiments can be accomplished by program instructions related hardware, and the foregoing program can be stored in a computer readable storage medium; when the program is executed, the steps of the above method embodiments are executed; the foregoing storage medium includes: various media that can store program codes, such as a ROM, a RAM, a magnetic disk, or an optical disc.

Finally, it should be noted that the above embodiments are only used to illustrate the technical solutions of the present invention, rather than limiting the same; although the present invention has been described in detail with reference to the foregoing embodiments, those of ordinary skill in the art should understand that it is still possible to modify the technical solutions described in the foregoing embodiments or equivalently replace some or all of the technical features; and these modifications or replacements do not deviate the essence of the corresponding technical solutions from the range of the technical solutions of the embodiments of the present invention.

What is claimed is:

1. A method for detecting a viscoelastic parameter of a viscoelastic medium, comprising:
    Applying a mechanical vibration at a single predetermined frequency to the viscoelastic medium to generate a shear wave in the viscoelastic medium;
    during propagation of the shear wave in the viscoelastic medium, emitting single-source ultrasonic waves to the viscoelastic medium and receiving ultrasonic echo signals;
    acquiring maximum displacement data of the shear wave at various depths according to the ultrasonic echo signals, each of the maximum displacement data representing a maximum oscillation amplitude of the shear wave when the shear wave propagates to different depths in the viscoelastic medium;
    fitting each of the maximum displacement data to obtain a maximum displacement attenuation curve as follows:

$$y=ax^2+bx+c$$

where the a, b and c are parameters to be determined, y is a maximum displacement data of the shear wave at a depth, and x is a propagation distance of the shear wave; and
    determining the viscoelastic parameter of the viscoelastic medium according to the maximum displacement attenuation curve, the viscoelastic parameter being a coefficient corresponding to a highest power variable of the maximum displacement attenuation curve.

2. The method according to claim 1, wherein before the acquiring maximum displacement data of the shear wave at various depths according to the ultrasonic echo signals, the method further comprises:
    performing at least one of the following signal processings on the ultrasonic echo signals: time domain cross correlation, spectral cross correlation, square error sum, speckle tracking, scale invariant feature point tracking, dynamic programming, zero cross tracking, and peak search.

3. The method according to claim 1, wherein the fitting each of the maximum displacement data to obtain a maximum displacement attenuation curve comprises:
    performing a filtering processing on each of the maximum displacement data in time domain and frequency domain to exclude an abnormal datum in each of the maximum displacement data;
    performing a polynomial fitting on each of the maximum displacement data after excluding the abnormal datum to obtain the maximum displacement attenuation curve.

4. The method according to claim 1, wherein the method further comprises:
    acquiring an elastic parameter of the viscoelastic medium according to the ultrasonic echo signals;
    determining a degree of fibrosis of the viscoelastic medium based on the elastic parameter and the viscoelastic parameter.

5. The method according to claim 2, wherein the method further comprises:
    acquiring an elastic parameter of the viscoelastic medium according to the ultrasonic echo signals;
    determining a degree of fibrosis of the viscoelastic medium based on the elastic parameter and the viscoelastic parameter.

6. The method according to claim 3, wherein the method further comprises:
    acquiring an elastic parameter of the viscoelastic medium according to the ultrasonic echo signals;
    determining a degree of fibrosis of the viscoelastic medium based on the elastic parameter and the viscoelastic parameter.

7. A device for detecting a viscoelastic parameter of a viscoelastic medium, comprising:
    a control host and a probe, the probe including a vibrator and an ultrasonic transducer, wherein
    the vibrator, under the control of the control host, applies a mechanical vibration at a single predetermined frequency to the viscoelastic medium to generate a shear wave in the viscoelastic medium;
    during propagation of the shear wave in the viscoelastic medium, the ultrasonic transducer, under the control of the control host, emitting single-source ultrasonic waves to the viscoelastic medium and receives ultrasonic echo signals; and
    the control host comprises:
    a first acquiring module that is configured to acquire maximum displacement data of the shear wave at various depths according to the ultrasonic echo signals, each of the maximum displacement data representing a maximum oscillation amplitude of the shear wave when the shear wave propagates to different depths in the viscoelastic medium;
    a computing module that is configured to fit the maximum displacement data to obtain a maximum displacement attenuation curve as follows:

$$y=ax^2+bx+c$$

where the a, b and c are parameters to be determined, y is a maximum displacement data of the shear wave at a depth, and x is a propagation distance of the shear wave; and a first determining module that is configured to determine the viscoelastic parameter of the viscoelastic medium according to the maximum displacement attenuation curve, the viscoelastic parameter being a coefficient corresponding to a highest power variable of the maximum displacement attenuation curve.

8. The device according to claim 7, wherein the control host further comprises:
a processing module that is configured to perform at least one of the following signal processings on the ultrasonic echo signals: time domain cross correlation, spectral cross correlation, square error sum, speckle tracking, scale invariant feature point tracking, dynamic programming, zero cross tracking, and peak search.

9. The device according to claim 7, wherein the computing module comprises:
a first computing unit that is configured to perform a filtering processing on each of the maximum displacement data in time domain and frequency domain, to exclude an abnormal datum in each of the maximum displacement data;
a second computing unit that is configured to perform a polynomial fitting on each of the maximum displacement data after excluding the abnormal datum to obtain the maximum displacement attenuation curve.

10. The device according to claim 7, wherein the control host further comprises:
a second acquiring module that is configured to acquire an elastic parameters of the viscoelastic medium according to the ultrasonic echo signals; and
a second determining module that is configured to determine a degree of fibrosis of the viscoelastic medium based on the elastic parameter and the viscoelastic parameter.

11. The device according to claim 8, wherein the control host further comprises:
a second acquiring module that is configured to acquire an elastic parameters of the viscoelastic medium according to the ultrasonic echo signals; and
a second determining module that is configured to determine a degree of fibrosis of the viscoelastic medium based on the elastic parameter and the viscoelastic parameter.

12. The device according to claim 9, wherein the control host further comprises:
a second acquiring module that is configured to acquire an elastic parameters of the viscoelastic medium according to the ultrasonic echo signals; and
a second determining module that is configured to determine a degree of fibrosis of the viscoelastic medium based on the elastic parameter and the viscoelastic parameter.

* * * * *